US008688190B2

(12) United States Patent
Libbus et al.

(10) Patent No.: US 8,688,190 B2
(45) Date of Patent: Apr. 1, 2014

(54) ADHERENT DEVICE FOR SLEEP DISORDERED BREATHING

(75) Inventors: Imad Libbus, Saint Paul, MN (US); Yatheendhar D. Manicka, Woodbury, MN (US); Mark J. Bly, Falcon Heights, MN (US)

(73) Assignee: Corventis, Inc., San Jose, CA (US)

( * ) Notice: Subject to any disclaimer, the term of this patent is extended or adjusted under 35 U.S.C. 154(b) by 0 days.

(21) Appl. No.: 13/543,660

(22) Filed: Jul. 6, 2012

(65) Prior Publication Data
US 2012/0277549 A1 Nov. 1, 2012

Related U.S. Application Data

(63) Continuation of application No. 12/209,292, filed on Sep. 12, 2008, now Pat. No. 8,249,686.

(60) Provisional application No. 60/972,537, filed on Sep. 14, 2007, provisional application No. 60/972,363, filed on Sep. 14, 2007, provisional application No. 60/972,336, filed on Sep. 14, 2007, provisional application No. 61/055,656, filed on May 23, 2008, provisional application No. 61/055,666, filed on May 23, 2008.

(51) Int. Cl.
*A61B 5/053* (2006.01)
*A61B 5/113* (2006.01)

(52) U.S. Cl.
USPC ............ 600/391; 600/536; 600/547; 600/393

(58) Field of Classification Search
USPC ................ 600/372, 382, 391–393, 547, 529, 600/533–536, 301
See application file for complete search history.

(56) References Cited

U.S. PATENT DOCUMENTS

| | | | |
|---|---|---|---|
| 6,267,730 B1 * | 7/2001 | Pacunas | 600/534 |
| 6,416,471 B1 * | 7/2002 | Kumar et al. | 600/300 |
| 6,577,897 B1 * | 6/2003 | Shurubura et al. | 600/547 |
| 7,942,824 B1 * | 5/2011 | Kayyali et al. | 600/538 |
| 8,116,841 B2 * | 2/2012 | Bly et al. | 600/391 |
| 8,249,686 B2 * | 8/2012 | Libbus et al. | 600/391 |
| 2002/0099277 A1 * | 7/2002 | Harry et al. | 600/301 |
| 2005/0080463 A1 * | 4/2005 | Stahmann et al. | 607/62 |
| 2006/0041280 A1 * | 2/2006 | Stahmann et al. | 607/17 |
| 2006/0064030 A1 * | 3/2006 | Cosentino et al. | 600/547 |
| 2008/0033260 A1 | 2/2008 | Sheppard et al. | |

* cited by examiner

*Primary Examiner* — Lee S Cohen
*Assistant Examiner* — Erin M Cardinal
(74) *Attorney, Agent, or Firm* — Kilpatrick Townsend & Stockton LLP

(57) ABSTRACT

An adherent device is configured to adhere to the skin of the patient with an adherent patch, for example breathable tape, coupled to at least four electrodes. The device comprises impedance circuitry coupled to the at least four electrodes and configured to measure respiration of the patient to detect sleep apnea and/or hypopnea. The impedance circuitry may be used to measure hydration of the patient. An accelerometer can be mechanically coupled to the adherent patch such that the accelerometer can be coupled to and move with the skin of the patient. Electrocardiogram circuitry to generate an electrocardiogram signal may be coupled to at least two of the at least four electrodes to detect the sleep apnea and/or hypopnea.

30 Claims, 11 Drawing Sheets

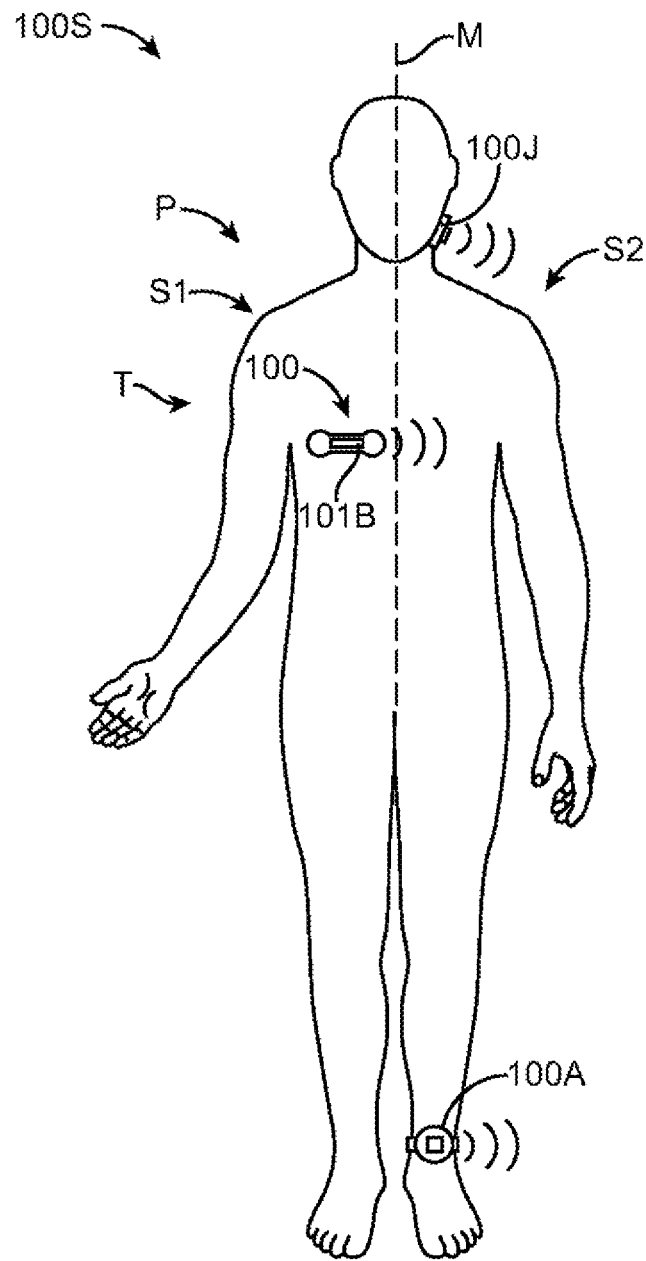
FIG. 1A1

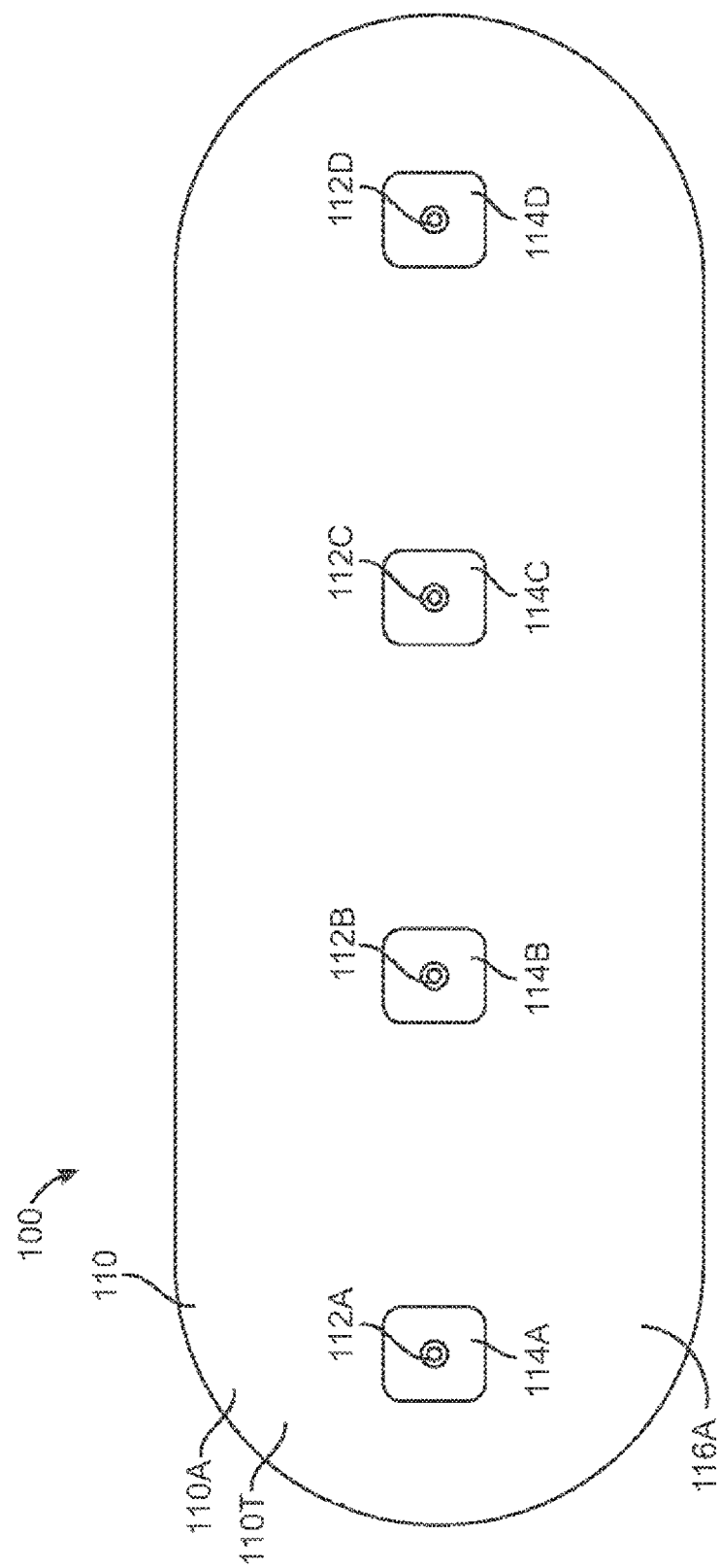

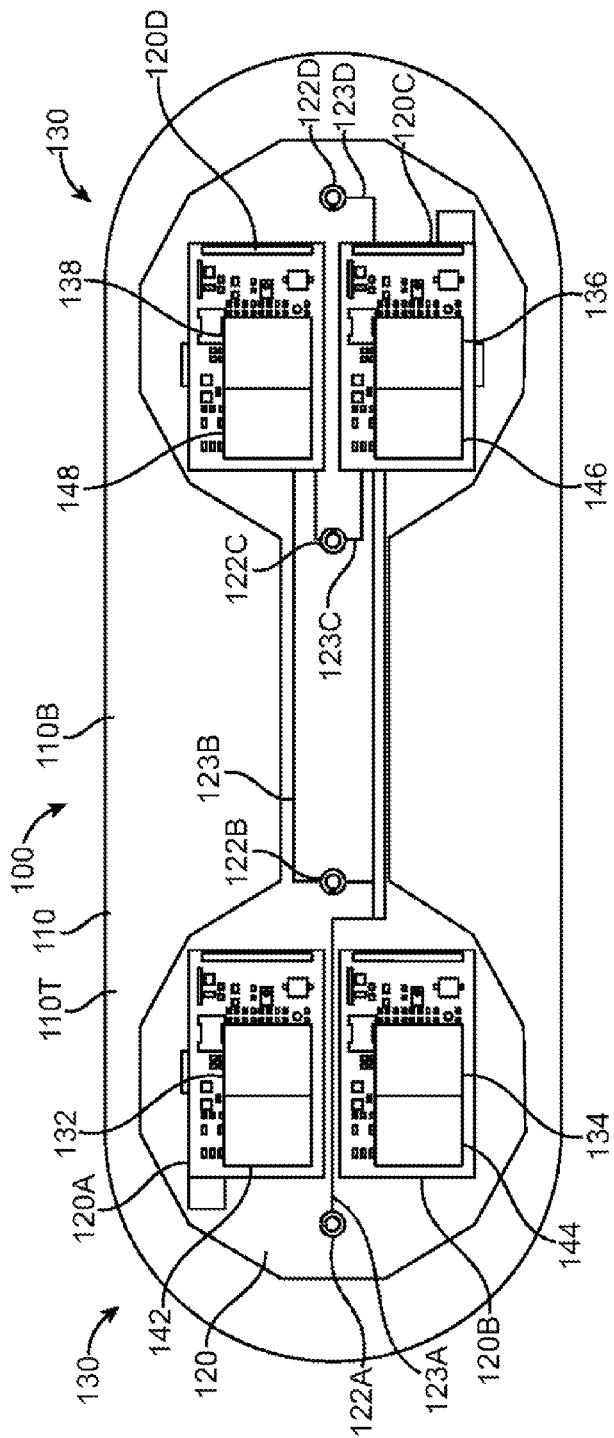
FIG. 1D
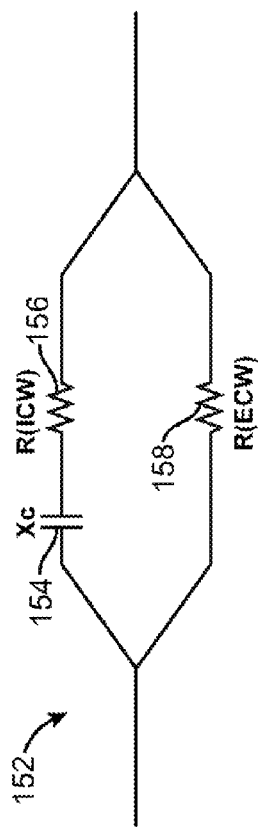
FIG. 1D1

ADHERENT DEVICE FOR SLEEP DISORDERED BREATHING

CROSS-REFERENCES TO RELATED APPLICATIONS

The present application is a continuation of U.S. patent application Ser. No. 12/209,292 filed Sep. 12, 2008, which issued Aug. 21, 2012 as U.S. Pat. No. 8,249,686 titled "Adherent Device For Sleep Disordered Breathing", and which claims the benefit under 35 USC 119(e) of U.S. Provisional Application Nos. 60/972,537, 60/972,363, and 60/972,336 all filed Sep. 14, 2007, and 61/055,656 and 61/055,666 both filed May. 23, 2008; the full disclosures of which are incorporated herein by reference in their entirety.

The subject matter of the present application is related to the following applications: 60/972,512; 60/972,329; 60/972,354; 60/972,616; 60/972,343; 60/972,581; 60/972,629; 60/972,316; 60/972,333; 60/972,359; 60/972,340 all of which were filed on Sep. 14, 2007; 61/046,196 filed Apr. 18, 2008; 61/047,875 filed Apr. 25, 2008; 61/055,645 and 61/055,662 both filed May 23, 2008; and 61/079,746 filed Jul. 10, 2008.

The following applications are being filed concurrently with the present application, on Sep. 12, 2008: U.S. patent application Ser. No. 12/209,279 entitled "Multi-Sensor Patient Monitor to Detect Impending Cardiac Decompensation Prediction"; U.S. patent application Ser. No. 12/209,288 entitled "Adherent Device with Multiple Physiological Sensors"; U.S. patent application Ser. No. 12/209,430 entitled "Injectable Device for Physiological Monitoring"; U.S. patent application Ser. No. 12/209,479 entitled "Injectable Physiological Monitoring System"; U.S. patent application Ser. No. 12/209,262 entitled "Adherent Device for Cardiac Rhythm Management"; U.S. patent application Ser. No. 12/209,268 entitled "Adherent Device for Respiratory Monitoring"; U.S. patent application Ser. No. 12/209,269 entitled "Adherent Athletic Monitor"; U.S. patent application Ser. No. 12/209,259 entitled "Adherent Emergency Monitor";U.S. patent application Ser. No. 12/209,273 entitled "Adherent Device with Physiological Sensors"; U.S. patent application Ser. No. 12/209,276 entitled "Medical Device Automatic Start-up upon Contact to Patient Tissue"; U.S. patent application Ser. No. 12/210,078 entitled "System and Methods for Wireless Body Fluid Monitoring"; U.S. patent application Ser. No. 12/209,265 entitled "Adherent Cardiac Monitor with Advanced Sensing Capabilities"; U.S. patent application Ser. No. 12/209,278 entitled "Dynamic Pairing of Patients to Data Collection Gateways";U.S. patent application Ser. No. 12/209,508 entitled "Adherent Multi-Sensor Device with Implantable Device Communications Capabilities"; U.S. patent application Ser. No. 12/209,528 entitled "Data Collection in a Multi-Sensor Patient Monitor";U.S. patent application Ser. No. 12/209,271 entitled "Adherent Multi-Sensor Device with Empathic Monitoring"; U.S. patent application Ser. No. 12/209,274 entitled "Energy Management for Adherent Patient Monitor"; and U.S. patent application Ser. No. 12/209,294 entitled "Tracking and Security for Adherent Patient Monitor."

BACKGROUND OF THE INVENTION

1. Field of the Invention

The present invention relates to patient monitoring. Although embodiments make specific reference to monitoring impedance and electrocardiogram signals with an adherent device, the system methods and device described herein may be applicable to many applications in which physiological monitoring is used, for example wireless physiological monitoring for extended periods.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital. One example of a device to provide long term monitoring of a patient is the Holter monitor, or ambulatory electrocardiography device, which may use electrodes attached to the skin to measure electrocardiogram signals from the patient.

In addition to measuring heart signals with electrocardiograms, known physiologic measurements include impedance measurements. For example, transthoracic impedance measurements can be used to measure hydration and respiration. Although transthoracic measurements can be useful, such measurements may use electrodes that may be somewhat uncomfortable and/or cumbersome for the patient to wear. In at least some instances, electrodes that are held against the skin of the patient can become detached and/or dehydrated, such that the electrodes must be replaced, thereby making long term monitoring more difficult.

Work in relation to embodiments of the present invention suggests that known methods and apparatus for long term monitoring of patients may be less than ideal. At least some of the known devices may not collect the right kinds of data to treat patients optimally. For example, although successful at detecting and storing electrocardiogram signals, devices such as the Holter monitor can be somewhat bulky and may not collect all of the kinds of data that would be ideal to diagnose and/or treat a patient for apnea and/or hypopnea. In at least some instances, devices that are worn by the patient may be somewhat uncomfortable, which may lead to patients not wearing the devices and not complying with direction from the health care provider, such that data collected may be less than ideal.

Although some current instrumentation for sleep studies, such as polysomnography, may be capable of determining an apnea hypopnea index (hereinafter "AHI"), work in relation to embodiments of the present invention suggests that current polysomnogram instrumentation may be les than ideal. To record physiological variable with a polysomnogram, a patient may sleep in a clinic while wearing skin electrodes that are tethered to a data acquisition system. Such use of skin electrodes tethered to a data acquisition system can be uncomfortable, relatively expensive, and may not duplicate normal sleep conditions, in at least some instances.

Although implantable devices may be used in some instances, many of the implantable devices can be invasive and/or costly, and may suffer at least some of the shortcomings of known wearable devices. In addition, implantation may require surgery that can subject an already frail patient to additional and undesirable physiologic stress.

Therefore, a need exists for improved patient monitoring. Ideally, such improved patient monitoring would avoid at least some of the short-comings of the present methods and devices.

2. Description of the Background Art

The following U.S. Patents and Publications may describe relevant background art: U.S. Pat. Nos. 4,121,573; 4,955,381;

4,981,139; 5,080,099; 5,353,793; 5,511,553; 5,544,661; 5,558,638; 5,724,025; 5,772,586; 5,862,802; 6,047,203; 6,117,077; 6,129,744; 6,225,901; 6,385,473; 6,416,471; 6,454,707; 6,494,829; 6,527,711; 6,527,729; 6,551,252; 6,595,927; 6,595,929; 6,605,038; 6,641,542; 6,645,153; 6,821,249; 6,980,851; 7,020,508; 7,041,062; 7,054,679; 7,153,262; 7,206,630; 7,297,119; 2003/0092975; 2005/0113703; 2005/0131288; 2005/0137464; 2005/0277841; 2005/0277842; 2006/0010090; 2006/0089679; 2006/122474; 2006/0155183; 2006/0173257; 2006/0195144; 2006/0224051; 2006/0224072; 2006/0264730; 2006/0173269; 2006/0161205; 2007/0021678; 2006/0031102; 2007/0038038; 2007/0073132; 2007/0123756; 2007/0129643; 2007/0150008; and 2007/0255531.

BRIEF SUMMARY OF THE INVENTION

The present invention relates to patient monitoring. Although embodiments make specific reference to monitoring impedance and electrocardiogram signals with an adherent device, the system methods and device described herein may be applicable to any application in which physiological monitoring is used, for example wireless physiological monitoring for extended periods. An adherent device is configured to adhere to the skin of the patient with an adherent patch, for example breathable tape, coupled to at least four electrodes. The device comprises impedance circuitry coupled to the at least four electrodes and configured to measure respiration of the patient to detect sleep apnea and/or hypopnea. An accelerometer can be mechanically coupled to the adherent patch such that the accelerometer can be coupled to and move with the skin of the patient, thereby providing an accurate and reliable measurement of the orientation and/or activity of the patient, which can be helpful in determining that the patient is asleep. Electrocardiogram circuitry to generate an electrocardiogram signal may be coupled to at least two of the at least four electrodes, such that the sleep apnea and/or hypopnea can be detected in response to a heart rate variability from the electrocardiogram signal. For example, a sleep apnea and/or hypopnea can result in an increased heart rate to deliver oxygen to tissues.

In a first aspect, embodiments of the present invention provide an adherent device to monitor a sleep apnea and/or hypopnea of a patient. The device comprises an adhesive patch to adhere to a skin of the patient. At least four electrodes are connected to the patch and capable of electrically coupling to the patient. Impedance circuitry is coupled to the at least four electrodes to measure an impedance signal of the patient. A processor system comprises a tangible medium configured to determine a respiration rate and detect the apnea and/or hypopnea in response to the impedance signal. This use of the impedance signal to detect the apnea and/or hypopnea of the patient provides accurate detection of apnea and/or hypopnea and allows the device to be compact and comfortably worn when adhered to the patient.

In many embodiments, the processor system is configured to determine an apnea hypopnea index of the patient in response to the impedance signal. The impedance circuitry may be configured to measure extra cellular fluid of the patient with at least one frequency within a range from about 0.5 kHz to about 200 kHz, and the impedance circuitry can be configured to determine a respiration of the patient.

In many embodiments, the processor system is configured to control a collection and transmission of data from the impedance circuitry.

In many embodiments, an accelerometer is mechanically coupled to a second adhesive patch to generate an accelerometer signal when the second adhesive patch is adhered to the skin of the patient. The second adhesive patch can be configured to adhere to at least one of an ankle, a leg a foot, or a jaw of the patient. The processor system can be configured to detect at least one of a restless leg or a bruxation of the patient in response to the accelerometer signal. The accelerometer may be coupled to wireless communication circuitry supported with the second patch to transmit the accelerometer signal to the processor system.

In many embodiments, electromyogram circuitry can be mechanically coupled to a second adhesive patch to generate an electromyogram signal when the second adhesive patch is adhered to the skin of the patient. The second adhesive patch can be configured to adhere to at least one of an ankle, a leg a foot, or a jaw of the patient. The processor system can be configured to detect at least one of a restless leg or a bruxation of the patient in response to the electromyogram signal. The second electromyogram circuitry can be coupled to wireless communication circuitry supported with the second patch to transmit the electromyogram signal to the processor system.

In many embodiments, an accelerometer is mechanically coupled to the adherent patch to generate an accelerometer signal when the adhesive patch is adhered to the skin of the patient, and can result in very reliable measurement of the patient as the accelerometer is mechanically coupled to the patch adhered to the patient. The processor system can be configured to determine that the patient is asleep in response to the accelerometer signal. The accelerometer may comprise at least one of a piezoelectric accelerometer, capacitive accelerometer or electromechanical accelerometer and wherein the accelerometer comprises a 3-axis accelerometer to measure at least one of an inclination, a position, an orientation or acceleration of the patient in three dimensions.

In many embodiments, electrocardiogram circuitry is coupled to at least two of the at least four electrodes to measure an electrocardiogram signal of the patient. The electrocardiogram signal may be used to detect the sleep apnea and/or hypopnea, for example in response to a heart rate variability from the electrocardiogram signal. This use of the at least two of the at least four electrodes, which are used for the impedance signal, may allow for the collection of additional patient data without increasing the footprint size of the patch adhered to the patient. The processor system can be configured to determine that the patient is asleep in response to the electrocardiogram signal and the accelerometer signal.

In many embodiments, the adhesive patch is mechanically coupled to the at least four electrodes, the impedance circuitry, the electrocardiogram circuitry, the accelerometer and at least one processor of the processor system, such that the patch is capable of supporting the at least four electrodes, the impedance circuitry, the electrocardiogram circuitry, the accelerometer and the at least one processor when the adherent patch is adhered to the skin of the patient.

In many embodiments, the adherent device comprising wireless communication circuitry coupled to the impedance circuitry to transmit the impedance signal to a remote center with a communication protocol.

In many embodiments, at least one processor of the processor system is supported with the adherent patch, and the at least one processor is configured to determine a respiration rate from the impedance signal and a heart rate from the electrocardiogram signal. This processing of the impedance signal to determine the respiration rate and processing of the electrocardiogram signal to determine heart rate can decrease data transmission requirements, for example so as to decrease bandwidth requirements of the communication system, while also allowing faster communication of relevant patient information to the remote center. The wireless communication circuitry can be configured to transmit at least one of the heart rate or the respiration rate to the remote center to determine the apnea hypopnea index.

In many embodiments, the adherent device comprises wireless communication circuitry coupled to the impedance circuitry to transmit the respiration rate to a remote center with a communication protocol. The wireless communication circuitry can be configured to transmit the respiration rate to the remote center with an intermediate device. The communication protocol may comprise at least one of Bluetooth, Zigbee, WiFi, WiMax, IR, a cellular protocol, amplitude modulation or frequency modulation. The intermediate device may comprise a data collection system to collect and/or store data from the wireless transmitter and wherein the data collection system is configured to communicate periodically with the remote center with wireless connection and/or wired communication. The communications protocol may comprise a two way protocol such that the remote center is capable of issuing commands to control data collection.

In many embodiments, the adhesive patch comprises a breathable tape, in which the breathable tape comprises a breathable material with an adhesive.

In another aspect, embodiments of the present invention provide a method of monitoring a sleep apnea of a patient. An adhesive patch is adhered to a skin of the patient to couple at least four electrodes to the skin of the patient. An impedance signal of the patient is measured with impedance circuitry coupled to the at least four electrodes. A respiration rate is determined from the impedance signal to detect an apnea and/or hypopnea of the patient.

In many embodiments, an apnea hypopnea index of the patient is determined in response to the impedance signal.

In many embodiments, an accelerometer signal is measured with an accelerometer in response to at least one of an activity, a restless leg, a bruxation or an orientation of the patient. The patient is determined to be asleep in response to the accelerometer signal.

In many embodiments, an electrocardiogram signal of the patient is measured with electrocardiogram circuitry coupled to at least two of the at least four electrodes. The adhesive patch may support the at least four electrodes, the impedance circuitry, the electrocardiogram circuitry and the accelerometer when the adherent patch is adhered to the skin of the patient.

In another aspect, embodiments of the present invention provide an adherent device to monitor an apnea and/or hypopnea of a patient for an extended period. The device comprises a breathable tape. The breathable tape comprises a porous material with an adhesive coating to adhere the breathable tape to a skin of the patient. At least one electrode is affixed to the breathable tape and capable of electrically coupling to a skin of the patient. At least one gel is disposed over a contact surface of the at least one electrode to electrically connect the electrode to the skin. A printed circuit board is supported with the breathable tape when the tape is adhered to the patient, the circuit board is connected to the at least one electrode with a flexible intermediate connector to provide strain relief between the printed circuit board and the at least one electrode. Electronic components are electrically connected to the printed circuit board and the at least one electrode to measure breathing of the patient and determine the apnea and/or hypopnea of the patient. A breathable cover is disposed over the circuit board and the electronic components, the breathable cover connected to at least one of the electronics components, the printed circuit board or the breathable tape.

In some embodiments, the breathable cover comprises a water resistant cover.

In many embodiments, the electronic components comprise a processor and wireless transmission circuitry. The processor comprises a tangible medium and may be configured to determine an apnea hypopnea index from the breathing of the patient. The wireless transmission circuitry can be configured to transmit the apnea hypopnea index from the processor to a remote center.

In many embodiments, the breathable tape, the at least one electrode, the at least one gel and the breathable cover are configured to couple the at least one electrode to the skin to measure breathing of the patient for at least one week and the extended period comprises at least one week. The breathable tape may comprise a stretchable breathable material with an adhesive, and the breathable cover may comprises a stretchable material connected to the breathable tape. Advantageously, the breathable tape and the breathable cover can stretch with the skin of the patient, for example when the patient moves. This stretching of the materials can minimize, and in some instances avoid, the formation of creases that may decrease the useful life of the patch and/or coupling of the at least one electrode to the patient. The printed circuit board may be slidably coupled with the breathable tape and the breathable cover such that the breathable tape and breathable cover are configured to stretch with the skin of the patient when the breathable tape is adhered to the skin of the patient. In specific embodiments, the electronics components are affixed to the printed circuit board, and the electronics components and the printed circuit board are disposed between the stretchable breathable material with the adhesive and the stretchable cover. The printed circuit board can be separated from the breathable tape with an air gap to allow the skin to release moisture and receive oxygen through the breathable tape and the breathable cover.

In many embodiments, an electronics housing is adhered to at least one of the electronics components or the printed circuit board, such that the electronics housing is disposed between the cover and electronics components. The electronics housing can be configured to keep water away from the at least one of the printed circuit board or the electronic components. This can be advantageous with an extended wear device as the patient may live a more normal life and can take a shower, for example, without destroying the electronic components and/or the printed circuit board.

In many embodiments, the electronics housing comprises at least one of a cover or a sealant configured to protect the at least one of the printed circuit board or the electronic components from water. The electronics housing may comprise a water resistant coating disposed over the at least one the electronic components or the printed circuit board so as to seal the at least one of electronic components or the printed circuitry board and inhibit water penetration. The water resistant coating may comprise a dip coating disposed over the at least one of the electronics components or the printed circuit board.

In many embodiments, a gel cover is positioned over the breathable tape. The gel cover may comprise a breathable material, for example a water resistant material, to inhibit moisture penetration from outside the patch into the at least one gel.

The gel cover many comprise a breathable material to inhibit a flow of the gel through the breathable tape and wherein the printed circuit board is located over the gel cover such that the gel cover is disposed between the breathable tape and the printed circuit board. In specific embodiments, he breathable tape comprises a tricot-knit polyester fabric backing and the gel cover comprises a polyurethane, nonwoven backing The breathable tape may comprise a first porosity and the gel cover may comprise a breathable tape with a second porosity, in which the second porosity is less than the first porosity to minimize, or even inhibit, flow of the gel through the breathable tape having the first porosity.

In many embodiments, the breathable tape, the adhesive coating, the at least one electrode and gel are separable from the printed circuit board, electronic components and cover, such that the printed circuit board, electronic components, housing and cover are reusable.

In many embodiments, the at least one electrode extends through at least one aperture in the breathable tape.

BRIEF DESCRIPTION OF THE DRAWINGS

FIG. 1A1 shows an adherent device system 1005 comprising a plurality of adherent devices simultaneously adhered to the patient, according to embodiments of the present invention;

FIG. 1B shows a bottom view of the adherent device as in FIG. 1A comprising an adherent patch;

FIG. 1D shows a printed circuit boards and electronic components over the adherent patch, as in FIG. 1C;

FIG. 1D1 shows an equivalent circuit that can be used to determine optimal frequencies for determining patient hydration, according to embodiments of the present invention;

DETAILED DESCRIPTION OF THE INVENTION

Figure 1A:
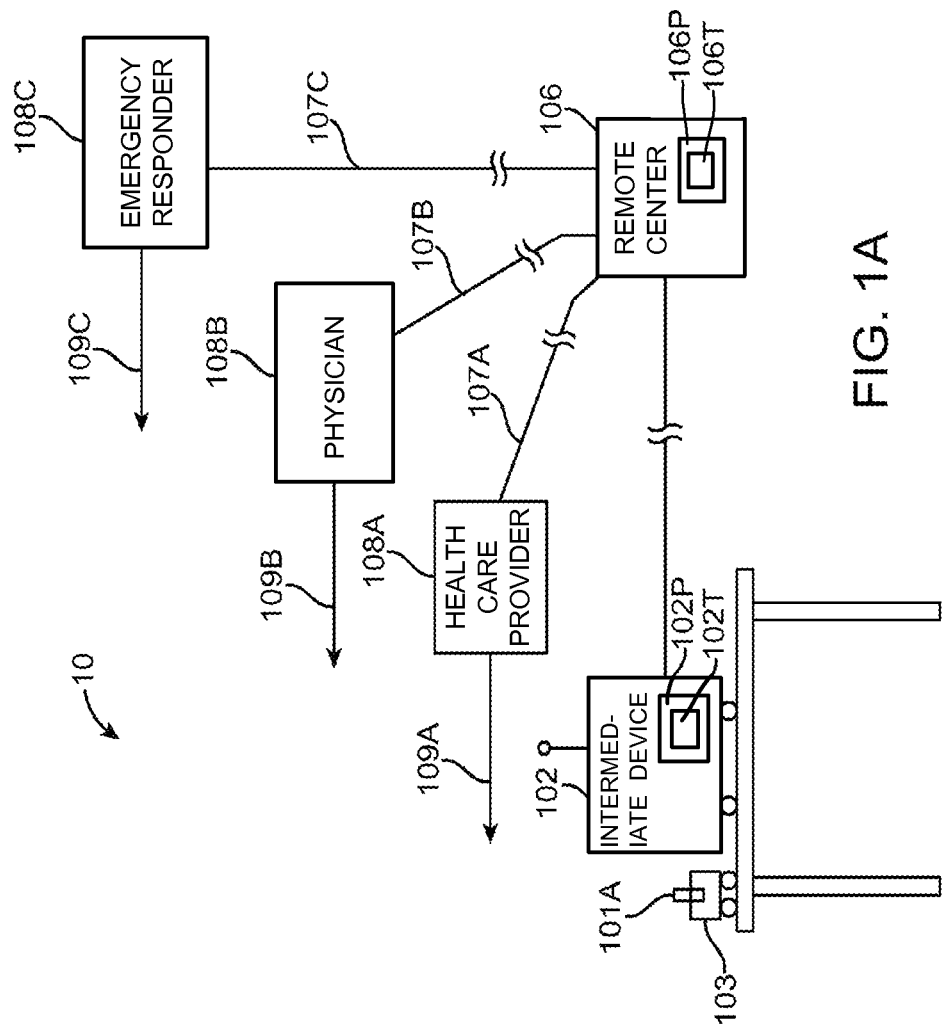
FIG. 1A shows a patient and a monitoring system comprising an adherent device, according to embodiments of the present invention.
Figure 1A:
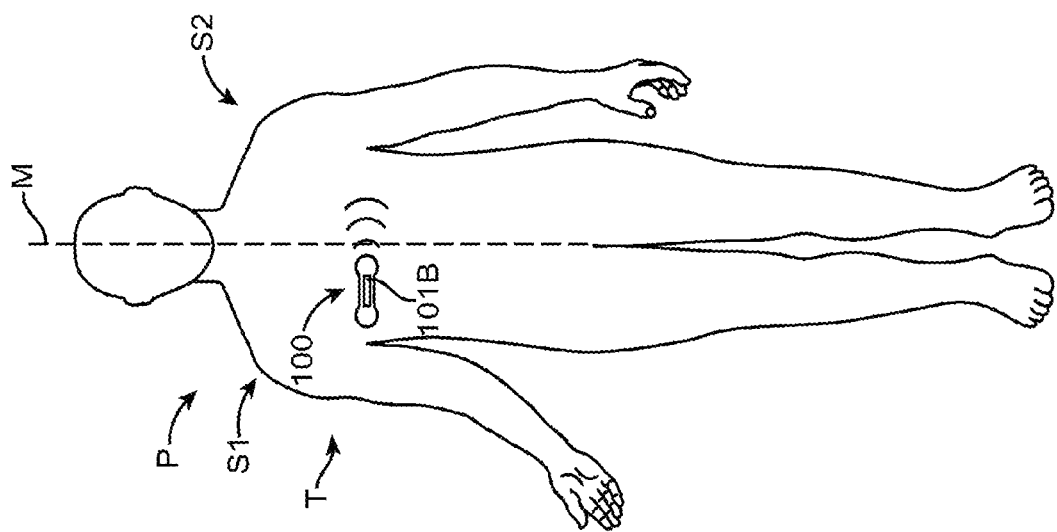

Embodiments of the present invention relate to patient monitoring. Although embodiments make specific reference to monitoring impedance, accelerometer and electrocardiogram signals with an adherent device, the system methods and device described herein may be applicable to any application in which physiological monitoring is used, for example wireless physiological monitoring for extended periods.

An adherent device is configured to adhere to the skin of the patient with an adherent patch, for example breathable tape, coupled to at least four electrodes. The device comprises impedance circuitry coupled to the at least four electrodes and configured to measure respiration of the patient to detect sleep apnea and/or hypopnea. Apnea can be an important hare failure comorbidity. The impedance circuitry may be used to measure hydration of the patient, which can be useful evaluating the physiologic status of the patient, for example in combination with the detected sleep apnea and/or hypopnea. An accelerometer can be mechanically coupled to the adherent patch such that the accelerometer can be coupled to and move with the skin of the patient, thereby providing an accurate and reliable measurement of the orientation and/or activity of the patient, which can be helpful in determining that the patient is asleep. The accelerometer can be mechanically coupled to the adherent patch such that the accelerometer can detect motion of the jaw and/or legs. Electrocardiogram circuitry to generate an electrocardiogram signal may be coupled to at least two of the at least four electrodes, such that the sleep apnea and/or hypopnea can be detected in response to a heart rate variability from the electrocardiogram signal.

Decompensation is failure of the heart to maintain adequate blood circulation. Although the heart can maintain at least some pumping of blood, the quantity is inadequate to maintain healthy tissues. Several symptoms can result from decompensation including pulmonary congestion, breathlessness, faintness, cardiac palpitation, edema of the extremities, and enlargement of the liver. Cardiac decompensation can result in slow or sudden death. Sudden Cardiac Arrest (hereinafter "SCA"), also referred to as sudden cardiac death, is an abrupt loss of cardiac pumping function that can be caused by a ventricular arrhythmia, for example ventricular tachycardia and/or ventricular fibrillation. Although decompensation and SCA can be related in that patients with decompensation are also at an increased risk for SCA, decompensation is primarily a mechanical dysfunction caused by inadequate blood flow, and SCA is primarily an electrical dysfunction caused by inadequate and/or inappropriate electrical signals of the heart.

In many embodiments, the adherent devices described herein may be used for 90 day monitoring, or more, and may comprise completely disposable components and/or reusable components, and can provide reliable data acquisition and transfer. In many embodiments, the patch is configured for patient comfort, such that the adherent patch can be worn and/or tolerated by the patient for extended periods, for example 90 days or more. The patch may be worn continuously for at least seven days, for example 14 days, and then replaced with another patch. Adherent devices with comfortable patches that can be worn for extended periods and in which patches can be replaced and the electronics modules reused are described in U.S. Pat. App. Nos. 60/972,537, entitled "Adherent Device with Multiple Physiological Sensors"; and 60/972,629, entitled "Adherent Device with Multiple Physiological Sensors", both filed on Sep. 14, 2007, the full disclosures of which have been previously incorporated herein by reference. In many embodiments, the adherent patch comprises a tape, which comprises a material, preferably breathable, with an adhesive, such that trauma to the patient skin can be minimized while the patch is worn for the extended period. The printed circuit board may comprise a flex printed circuit board that can flex with the patient to provide improved patient comfort.

FIG. 1A shows a patient P and a monitoring system 10. Patient P comprises a midline M, a first side S1, for example a right side, and a second side S2, for example a left side. Monitoring system 10 comprises an adherent device 100. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient.

Monitoring system 10 includes components to transmit data to a remote center 106. Remote center 106 can be located in a different building from the patient, for example in the same town as the patient, and can be located as far from the patient as a separate continent from the patient, for example the patient located on a first continent and the remote center located on a second continent. Adherent device 100 can communicate wirelessly to an intermediate device 102, for example with a single wireless hop from the adherent device on the patient to the intermediate device. Intermediate device 102 can communicate with remote center 106 in many ways, for example with an internet connection and/or with a cellular connection. In many embodiments, monitoring system 10 comprises a distributed processing system with at least one processor comprising a tangible medium of device 100, at least one processor 102P of intermediate device 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In some embodiments, remote center 106 receives the patient data and applies a patient evaluation algorithm, for example an algorithm to calculate the apnea hypopnea index. When a flag is raised, the center may communicate with the patient, hospital, nurse, and/or physician to allow for therapeutic intervention.

The adherent device may be affixed and/or adhered to the body in many ways. For example, with at least one of the following: an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches, and each of the replaceable patches may include a battery. The module may collect cumulative data for approximately 90 days and/or the entire adherent component (electronics+patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the patient.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, hear rate variability (HRV), heart rate turbulence (HRT), heart sounds (e.g. S3), respiratory sounds, blood pressure, activity, posture, wake/sleep, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

The adherent device can wirelessly communicate with remote center 106. The communication may occur directly (via a cellular or Wi-Fi network), or indirectly through intermediate device 102. Intermediate device 102 may consist of multiple devices, which can communicate wired or wirelessly to relay data to remote center 106.

In many embodiments, instructions are transmitted from remote site 106 to a processor supported with the adherent patch on the patient, and the processor supported with the patient can receive updated instructions for the patient treatment and/or monitoring, for example while worn by the patient.

FIG. 1A1 shows an adherent device system 100S comprising a plurality of adherent devices simultaneously adhered to the patient, for example adherent device 100, second adherent device 100J and third adherent device 100A. Adherent device system 100S may comprise wireless communication between and/or among devices adhered to the patient. Adherent device system 100S may comprise a component of system 10 described above. Second adherent device 100J can be disposed on the jaw of the patient to detect jaw movement and/or orientation, for example bruxation. Second adherent device 100J may comprise an accelerometer and/or electromyogram (EMG) circuitry comprising electrodes to detect patient jaw movement such as bruxation to determine the patient sleep status. Third adherent device 100A can be disposed on the patient to detect leg movement and/or orientation, for example on the leg, ankle and/or foot of the patient to detect restless leg syndrome. Third adherent device 100A may comprise an accelerometer and/or electromyogram (EMG) circuitry comprising electrodes to detect patient leg movement to determine the patient sleep status. Adherent device 100 may comprise an accelerometer and/or electromyogram circuitry comprising electrodes to detect patient motion, for example motion and/or orientation of the thorax.

FIG. 1B shows a bottom view of adherent device 100 as in FIG. 1A comprising an adherent patch 110. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

Figure 1C:
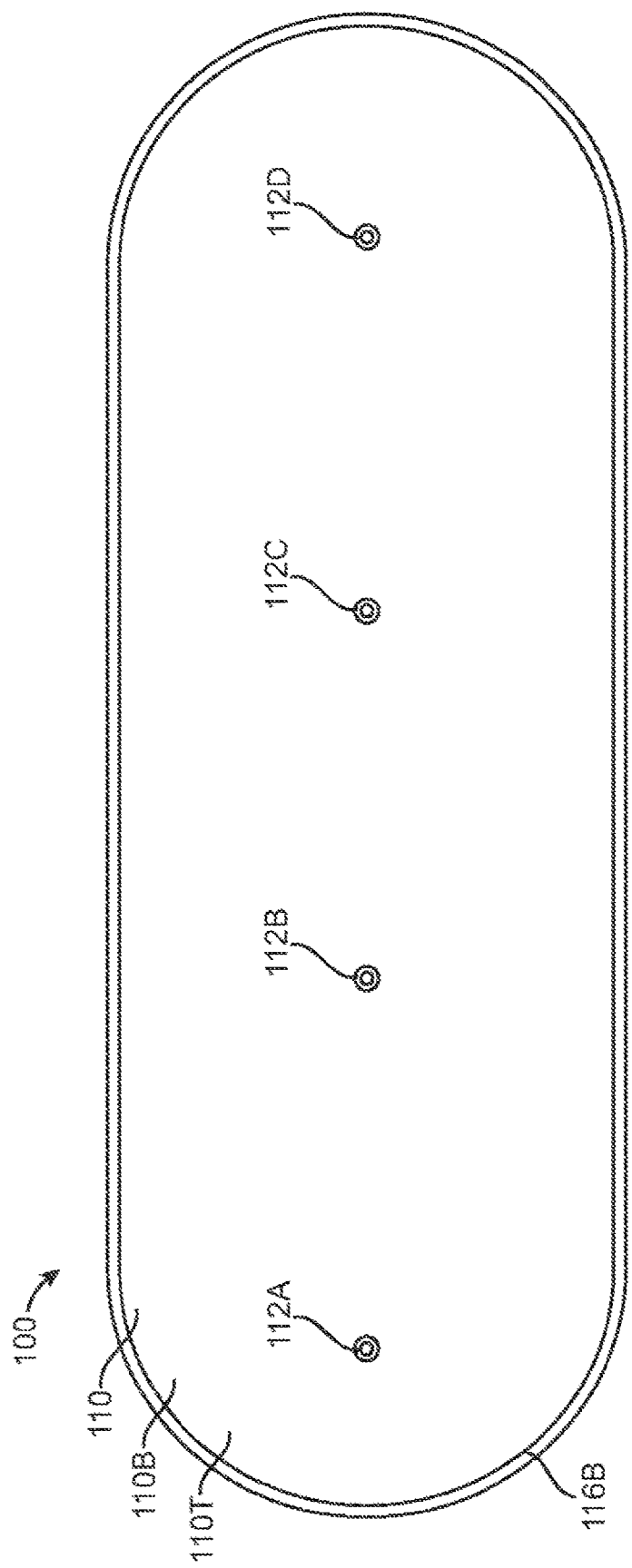
FIG. 1C shows a top view of the adherent patch, as in FIG. 1B.

FIG. 1C shows a top view of the adherent patch 100, as in FIG. 1B. Adherent patch 100 comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient. The PCB may comprise completely flex PCB, rigid PCB, rigid PCB combined flex PCB and/or rigid PCB boards connected by cable.

FIG. 1D shows a printed circuit boards and electronic components over adherent patch 110, as in FIG. 1A to 1C. In some embodiments, a printed circuit board (PCB), for example flex printed circuit board 120, may be connected to electrodes 112A, 112B, 112C and 112D with connectors 122A, 122B, 122C and 122D. Flex printed circuit board 120 can include traces 123A, 123B, 123C and 123D that extend to connectors 122A, 122B, 122C and 122D, respectively, on the flex PCB. Connectors 122A, 122B, 122C and 122D can be positioned on flex printed circuit board 120 in alignment with electrodes 112A, 112B, 112C and 112D so as to electrically couple the flex PCB with the electrodes. In some embodiments, connectors 122A, 122B, 122C and 122D may comprise insulated wires and/or a film with conductive ink that provide strain relief between the PCB and the electrodes. For example, connectors 122A, 122B, 122C and 122D may comprise a flexible polyester film coated with conductive silver ink. In some embodiments, additional PCB's, for example rigid PCB's 120A, 120B, 120C and 120D, can be connected to flex printed circuit board 120. Electronic components 130 can be connected to flex printed circuit board 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 138 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles.

Electronics circuitry 130 may comprise a temperature sensor, for example a thermistor in contact with the skin of the patient, and temperature sensor circuitry 144 to measure a temperature of the patient, for example a temperature of the skin of the patient. A temperature sensor may be used to determine the sleep and wake state of the patient. The temperature of the patient can decrease as the patient goes to sleep and increase when the patient wakes up.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vasodilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Processor 146 may comprise many known processors with real time clock and frequency generator circuitry, for example the PIC series of processors available from Microchip, of Chandler AZ. In some embodiments, processor 146 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

Electronics circuitry 130 may comprise electromyogram (hereinafter "EMG") circuitry 148 to measure muscle activity. EMG circuitry 148 can measure signals from muscles and may be connected to and/or comprise at least two of electrode 112A, electrode 112B, electrode 112C or electrode 112D. EMG circuitry 148 comprises an amplifier to amplify signals from contracting muscles so as to generate an EMG signal. EMG circuitry 148 can be connected to processor to send the EMG signal to the processor for storage and/or analysis.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, Zigbee, WiFi, WiMax, IR, amplitude modulation or frequency modulation. In many embodiments, the communications protocol comprises a two way protocol such that the remote center is capable of issuing commands to control data collection.

Intermediate device 102 may comprise a data collection system to collect and store data from the wireless transmitter. The data collection system can be configured to communicate periodically with the remote center. The data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electro-mechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or bioimpedance data, for example a respiration rate of the patient.

Impedance circuitry 136 can generate both hydration data and respiration data. In many embodiments, impedance circuitry 136 is electrically connected to electrodes 112A, 112B, 112C and 112D in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112B may comprise sense electrodes. The voltage measured by the sense electrodes can be used to measure the impedance of the patient and determine the respiration rate and/or hydration of the patient.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In some embodiments, ECG circuitry 138 can be connected to electrodes 112A and 112D so as to increase spacing of the electrodes. The inner electrodes may be positioned near the outer electrodes to increase the voltage of the ECG signal measured by ECG circuitry 138. In many embodiments, the ECG circuitry may measure the ECG signal from electrodes 112A and 112D when current is not passed through electrodes 112A and 112D, for example with switches as described in U.S. App. No. 60/972,527, the full disclosure of which has been previously incorporated herein by reference.

Figure 1E:
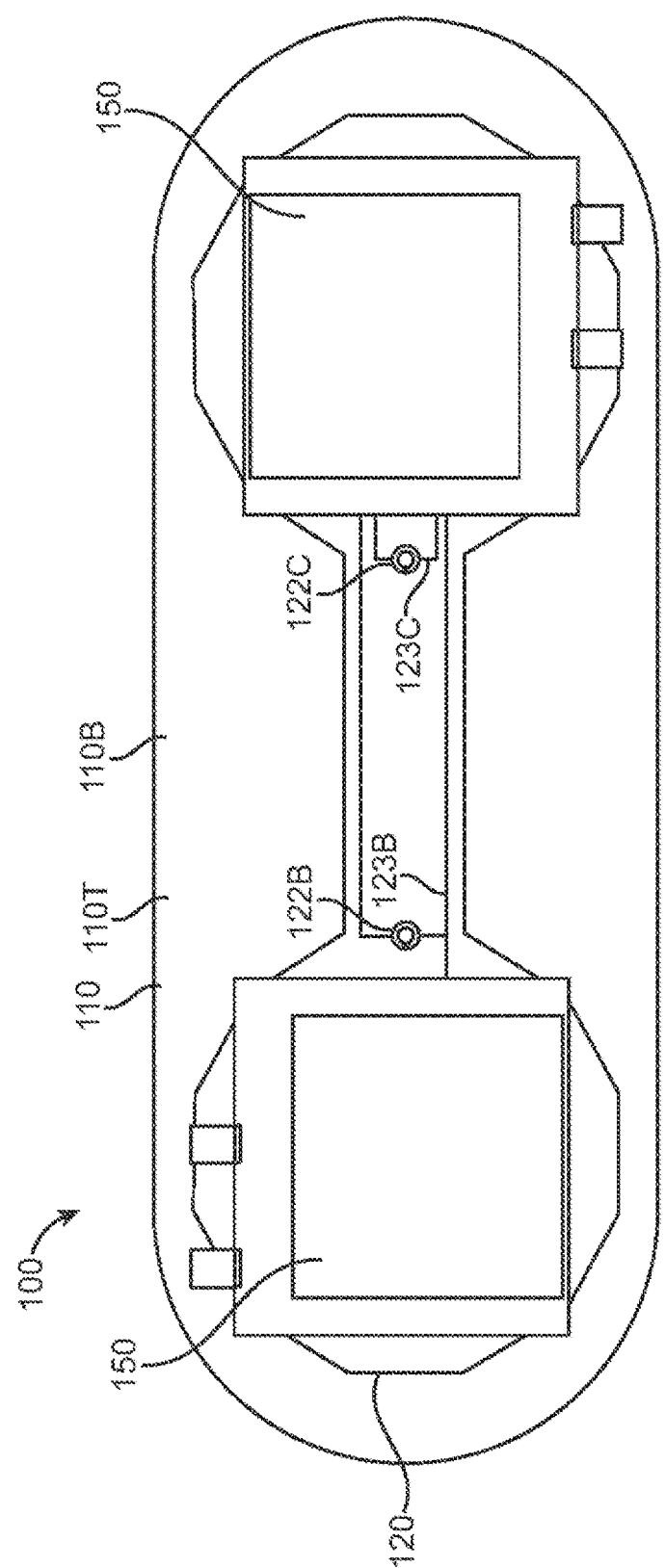
FIG. 1E shows batteries positioned over the printed circuit board and electronic components as in FIG. 1D.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
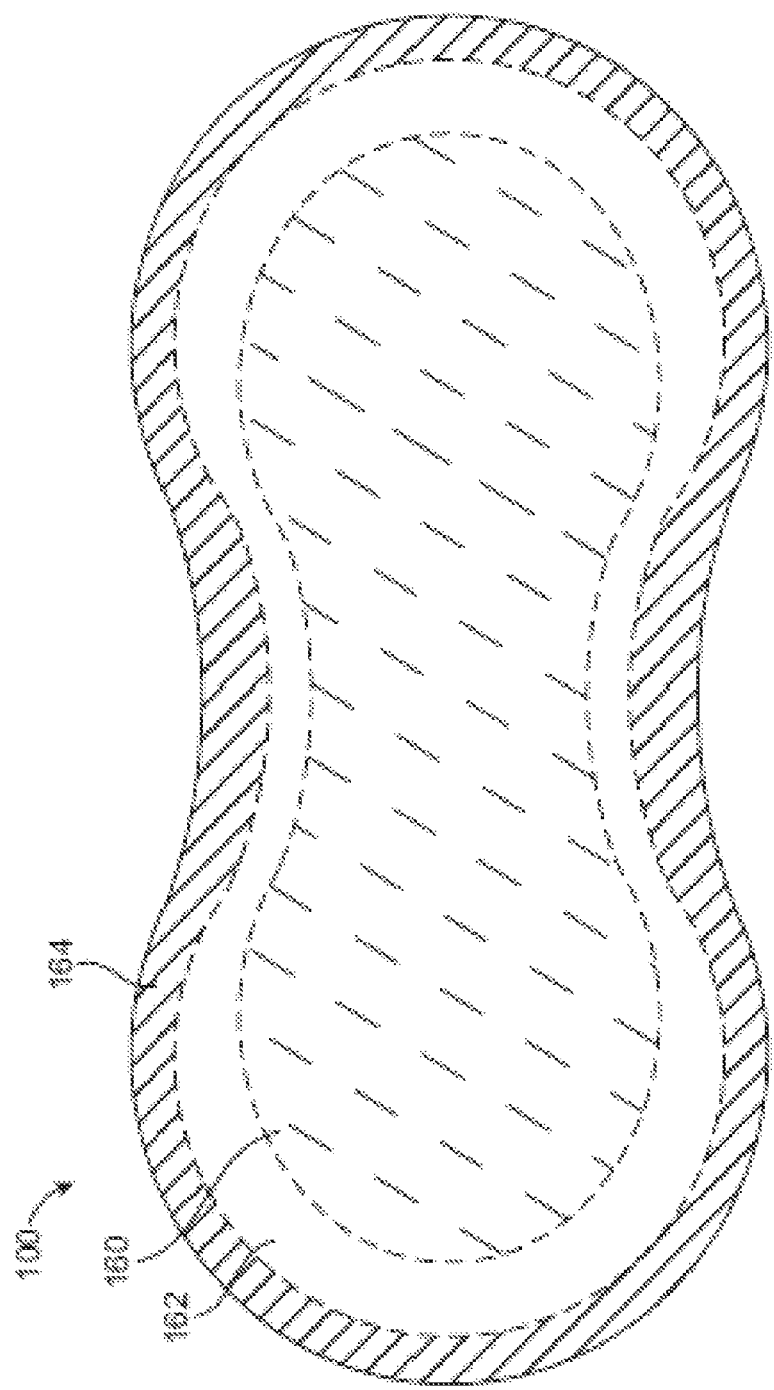
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIGS. 1A to 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adherent patch 110 with an adhesive 164 on an underside of cover 162. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, and/or elastane (Spandex). The breathable fabric may be coated to make it water resistant, waterproof, and/or to aid in wicking moisture away from the patch.

Figure 1H:
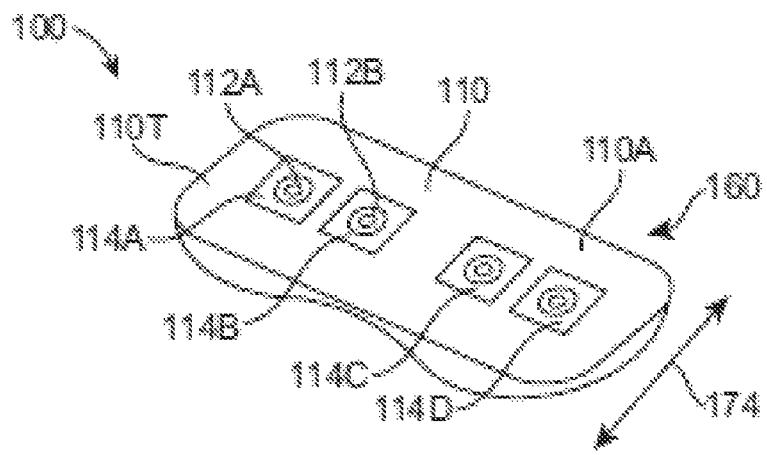
FIG. 1H shown a bottom isometric view of the adherent device as in FIGS. 1A to 1G.
Figure 1G:
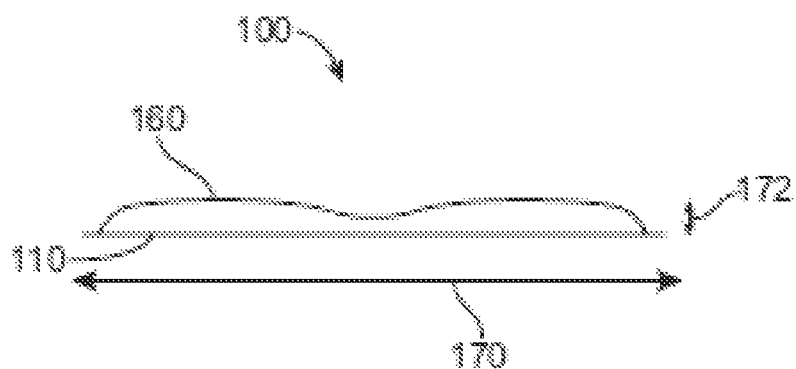
FIG. 1G shows a side view of the adherent device as in FIGS. 1A to 1F.

FIG. 1G shows a side view of adherent device 100 as in FIGS. 1A to 1F. Adherent device 100 comprises a maximum dimension, for example a length 170 from about 2 to 10 inches (from about 50 mm to about 250 mm), for example from about 4 to 6 inches (from about 100 mm to about 150 mm). In some embodiments, length 170 may be no more than about 6 inches (no more than about 150 mm). Adherent device 100 comprises a thickness 172. Thickness 172 may comprise a maximum thickness along a profile of the device. Thickness 172 can be from about 0.1 inches to about 0.4 inches (from about 5 mm to about 10 mm), for example about 0.3 inches (about 7.5 mm).

FIG. 1H shown a bottom isometric view of adherent device 100 as in FIGS. 1A to 1G. Adherent device 100 comprises a width 174, for example a maximum width along a width profile of adherent device 100. Width 174 can be from about 1 to about 4 inches (from about 25 mm to 100 mm), for example about 2 inches (about 50 mm).

Figure 1K:
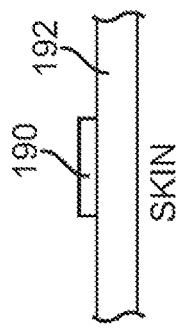
FIG. 1K shows at least one electrode configured to electrically couple to a skin of the patient through a breathable tape, according to embodiments of the present invention.
Figure 1I:
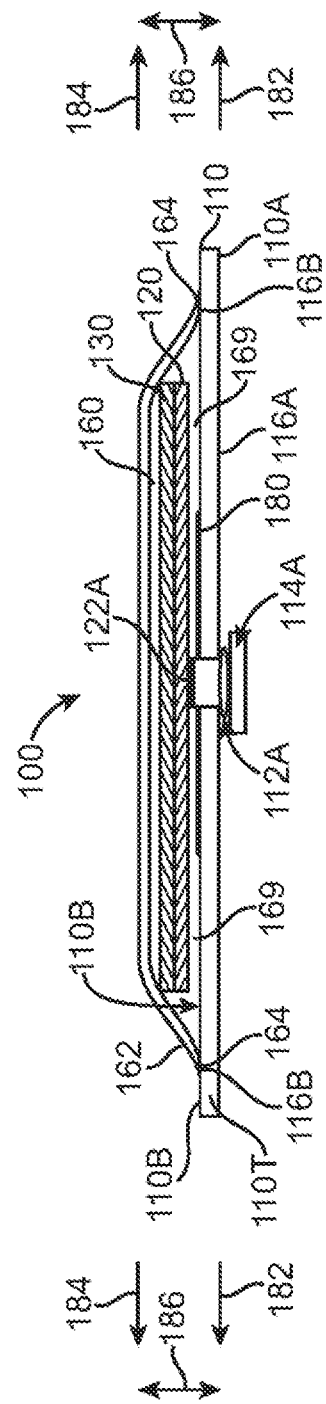
FIGS. 1I and 1J show a side cross-sectional view and an exploded view, respectively, of the adherent device as in FIGS. 1A to 1H.
Figure 1J:
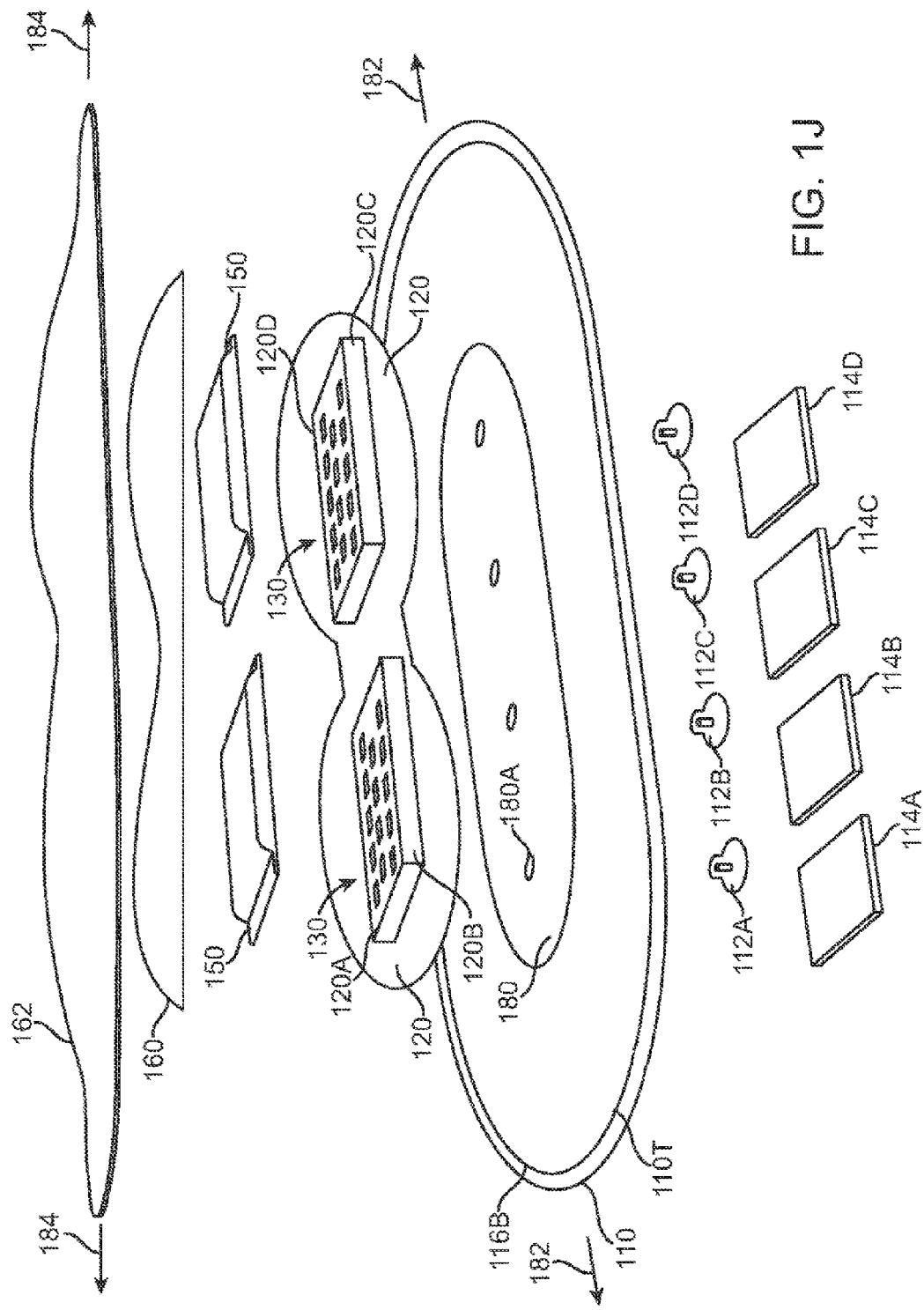

FIGS. 1I and 1J show a side cross-sectional view and an exploded view, respectively, of adherent device 100 as in FIGS. 1A to 1H. Device 100 comprises several layers. Gel 114A, or gel layer, is positioned on electrode 112A to provide electrical conductivity between the electrode and the skin. Electrode 112A may comprise an electrode layer. Adherent patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of adherent patch 110.

A gel cover 180, or gel cover layer, for example a polyurethane non-woven tape, can be positioned over patch 110 comprising the breathable tape. A PCB layer, for example flex printed circuit board 120, or flex PCB layer, can be positioned over gel cover 180 with electronic components 130 connected and/or mounted to flex printed circuit board 120, for example mounted on flex PCB so as to comprise an electronics layer disposed on the flex PCB layer. In many embodiments, the adherent device may comprise a segmented inner component, for example the PCB may be segmented to provide at least some flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex printed circuit board 120, so as to provide strain relive between the electrodes 112A, 112B, 112C and 112D and the PCB.

Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture, for example liquid water, from penetrating the gel cover into gel 114A while allowing moisture vapor from the gel, for example moisture vapor from the skin, to transmit through the gel cover.

In many embodiments, cover 162 can encase the flex PCB and/or electronics and can be adhered to at least one of the electronics, the flex PCB or adherent patch 110, so as to protect at least the electronics components and the PCB. Cover 162 can attach to adherent patch 110 with adhesive 116B. Cover 162 can comprise many known biocompatible cover materials, for example silicone. Cover 162 can comprise an outer polymer cover to provide smooth contour without limiting flexibility. In many embodiments, cover 162 may comprise a breathable fabric. Cover 162 may comprise many known breathable fabrics, for example breathable fabrics as described above. In some embodiments, the breathable cover may comprise a breathable water resistant cover. In some embodiments, the breathable fabric may comprise polyester, nylon, polyamide, and/or elastane (Spandex) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

The breathable cover 162 and adherent patch 110 comprise breathable tape can be configured to couple continuously for at least one week the at least one electrode to the skin so as to measure breathing of the patient. The breathable tape may comprise the stretchable breathable material with the adhesive and the breathable cover may comprises a stretchable water resistant material connected to the breathable tape, as described above, such that both the adherent patch and cover can stretch with the skin of the patient. Arrows 182 show stretching of adherent patch 110, and the stretching of adherent patch can be at least two dimensional along the surface of the skin of the patient. As noted above, connectors 122A, 122B, 122C and 122D between PCB 130 and electrodes 112A, 112B, 112C and 112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient. Cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along length 170 and width 174 with the skin of the patient, and stretching along length 170 can increase spacing between electrodes. Stretching of the cover and adherent patch 110, for example in two dimensions, can extend the time the patch is adhered to the skin as the patch can move with the skin such that the patch remains adhered to the skin Electronics housing 160 can be smooth and allow breathable cover 162 to slide over electronics housing 160, such that motion and/or stretching of cover 162 is slidably coupled with housing 160. The printed circuit board can be slidably coupled with adherent patch 110 that comprises breathable tape 110T, such that the breathable tape can stretch with the skin of the patient when the breathable tape is adhered to the skin of the patient, for example along two dimensions comprising length 170 and width 174. Electronics components 130 can be affixed to printed circuit board 120, for example with solder, and the electronics housing can be affixed over the PCB and electronics components, for example with dip coating, such that electronics components 130, printed circuit board 120 and electronics housing 160 are coupled together. Electronics components 130, printed circuit board 120, and electronics housing 160 are disposed between the stretchable breathable material of adherent patch 110 and the stretchable water resistant material of cover 160 so as to allow the adherent patch 110 and cover 160 to stretch together while electronics components 130, printed circuit board 120, and electronics housing 160 do not stretch substantially, if at all. This decoupling of electronics housing 160, printed circuit board 120 and electronic components 130 can allow the adherent patch 110 comprising breathable tape to move with the skin of the patient, such that the adherent patch can remain adhered to the skin for an extended time of at least one week, for example two or more weeks.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of printed circuit board 120 and electronic components 130, as indicated by arrows 186. Printed circuit board 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers.

The breathable tape of adherent patch 110 may comprise a first mesh with a first porosity and gel cover 180 may comprise a breathable tape with a second porosity, in which the second porosity is less than the first porosity to minimize, and even inhibit, flow of the gel through the breathable tape. The gel cover may comprise a polyurethane film with the second porosity.

In many embodiments, the adherent device comprises a patch component and at least one electronics module. The patch component may comprise adherent patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adherent patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. Two electronics modules can be provided, such that one electronics module can be worn by the patient while the other is charged, as described above. Monitoring with multiple adherent patches for an extended period is described in U.S. Pat. App. No. 60/972,537, the full disclosure of which has been previously incorporated herein by reference. Many patch components can be provided for monitoring over the extended period. For example, about 12 patches can be used to monitor the patient for at least 90 days with at least one electronics module, for example with two reusable electronics modules.

At least one electrode 112A can extend through at least one aperture 180A in the breathable tape 110 and gel cover 180.

In some embodiments, the adhesive patch may comprise a medicated patch that releases a medicament, such as antibiotic, beta-blocker, ACE inhibitor, diuretic, or steroid to reduce skin irritation. The adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin and electrode through the breathable tape, for example with the gel.

Second adherent device 100J and third adherent device 100A may comprise components similar to adherent device 100, described above. The processor of adherent device 100, described above may comprise a system controller to control communication and/or actions of first adherent device 100J and second device 100A, for example data collection and transmission. In many embodiments, data collected from second adherent device 100J and third adherent device 100A is sent wirelessly to device 100, which device 100 transmits the data to the intermediate device. In some embodiments, adherent device 100, second adherent device 100J and third adherent device 100A can each communicate data wirelessly with the intermediate device and may each receive instructions from the intermediate device.

Figure 2A:
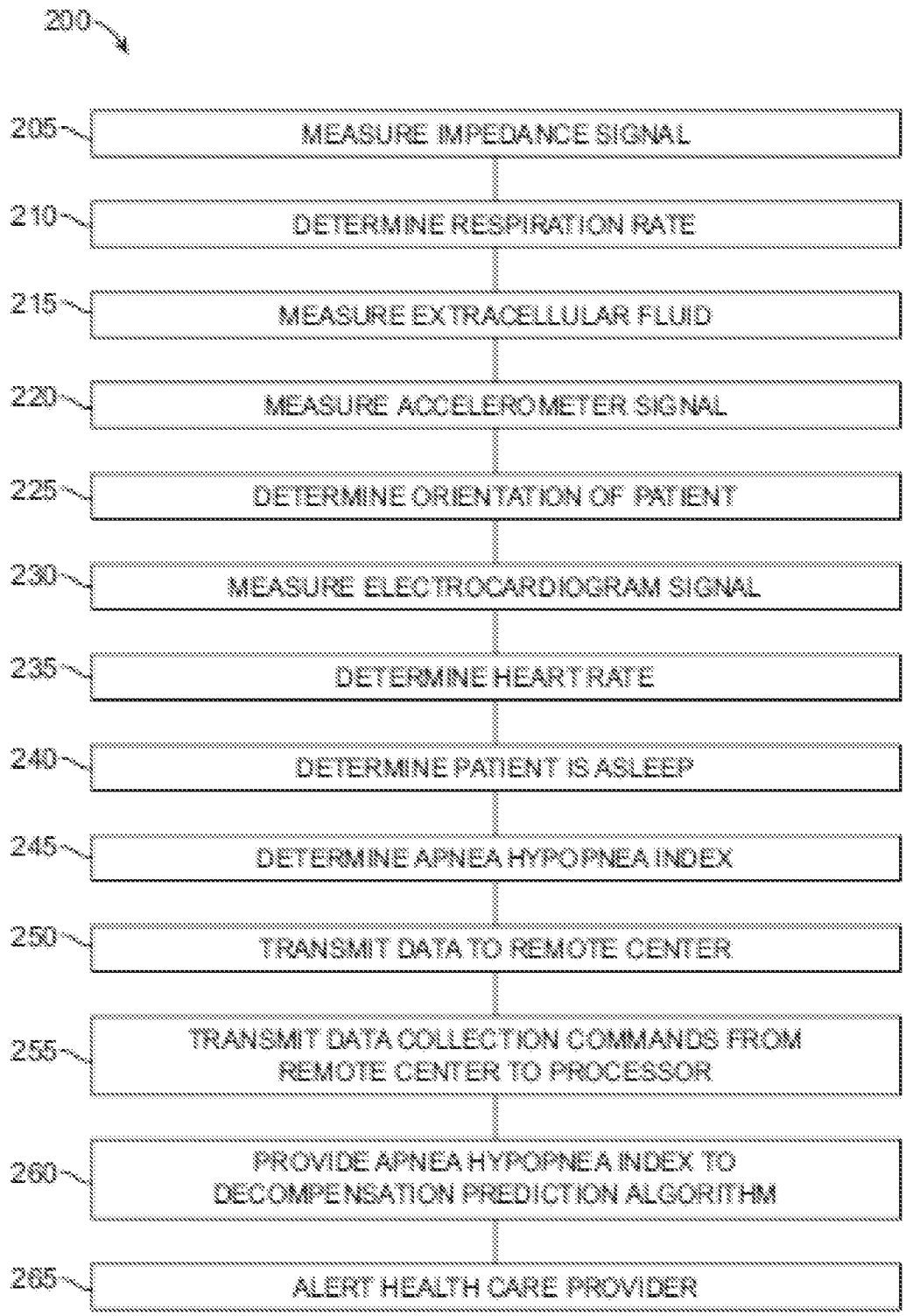
FIG. 2A shows a method of detecting apnea and/or hypopnea of a patient, according to embodiments of the present invention.

FIG. 2A shows a method 200 of monitoring a sleep apnea and/or hypopnea in a patient. Method 200 can be performed with the processor system, as described above. A step 205 measures an impedance signal of the patient. The impedance signal can be measured with a four pole impedance system as described above. A step 210 determines the respiration rate of the patient, for example from the impedance signal. Step 210 can be performed with at least one processor supported with the adhesive patch as descried above, so as to decrease data storage requirements of the electronic components supported with the adhesive patch. A step 215 measures extracellular fluid of the patient. The extracellular fluid can be used to monitor the hydration status of the patient and detect edema. A step 220 measures an accelerometer signal. The accelerometer signal can be generated with many accelerometers as described above, for example a three axis accelerometer. The accelerometer may correspond to patient activity, for example patient activity and orientation may be determined from the accelerometer signal. A step 225 determines orientation and/or activity of the patient, for example in response to the accelerometer signal. A step 230 measures an electrocardiogram signal of the patient. A step 235 determines a heart rate of the patient in response to the electrocardiogram signal. The heart rate of the patient can be determined with at least one processor supported with the adhesive patch, so as to decrease data storage requirements of the electronic components supported with the adhesive patch. A step 240 determines that the patient is asleep, for example in response to the respiration rate from the impedance signal, the activity and orientation of the patient from the accelerometer signal, and the heart rate from electrocardiogram signal. For example, a combination of low heart rate, low respiration rate, low activity amount and/or horizontal position can be used to determine the patient sleep state of the patient, for example that the patient is asleep A step 245 determines the apnea hypopnea index. In some embodiments, the apnea hypopnea index is determined at the remote center and/or the intermediate device in response to the heart rate and respiration rate determined with at least one processor supported with the adhesive patch. Known methods of calculating the apnea hypopnea index can be used, and at least some of the following U.S. patent publications and patents describe calculation of the apnea hypopnea index (AHI): 2007/0129643 (Kwok et al.); 2007/0123756 (Kitajima et al.); 2006/0173257 (Nagai et al.); and U.S. Pat. No. 6,641,542 (Cho et al.). A step 250 transmits patient information to the remote center, for example the patient apnea hypopnea index. A step 255 transmits data collection commands from the remote center to a processor supported with the adhesive patch. A step 260 provides the apnea hypopnea index to a decompensation prediction algorithm, for example as described in U.S. App. Nos. 60/972,512, entitled " Multi-Sensor Patient Monitor to Detect Impending Cardiac Decompensation"; and 61/035,970, entitled " Heart Failure Decompensation Prediction Based on Cardiac Rhythm", filed on Mar. 12, 2008; the full disclosures of which are incorporated by reference. A step 265 can alter a health care provider in response to one or more of the measured signals, for example the heart rate signal and/or the respiration rate signal, and provide the apnea hypopnea index to the treating physician and/or health care provider as a report.

The processor system, as described above, can be configured to perform the method 200, including many of the steps described above. It should be appreciated that the specific steps illustrated in FIG. 2A provide a particular method of monitoring a patient for sleep disordered breathing, according to an embodiment of the present invention. Other sequences of steps may also be performed according to alternative embodiments. For example, alternative embodiments of the present invention may perform the steps outlined above in a different order. Moreover, the individual steps illustrated in FIG. 2A may include multiple sub-steps that may be performed in various sequences as appropriate to the individual step. Furthermore, additional steps may be added or removed depending on the particular applications. One of ordinary skill in the art would recognize many variations, modifications, and alternatives.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A system to monitor a sleep apnea and/or hypopnea of a patient, the system comprising:
    an adhesive patch to adhere to a skin of the patient;
    at least four electrodes connected to the adhesive patch and capable of electrically coupling to the patient;
    impedance circuitry coupled to the at least four electrodes to measure an impedance signal of the patient; and
    a processor system comprising a tangible medium configured to determine a respiration rate and detect the apnea and/or hypopnea in response to the impedance signal, and to provide information about the apnea and/or hypopnea to an algorithm configured to predict decompensation.

2. The system of claim 1, wherein the processor system is configured to determine an apnea hypopnea index of the patient in response to the impedance signal and to provide the apnea hypopnea index to the algorithm configured to predict decompensation.

3. The system of claim 1 wherein the impedance circuitry is configured to measure extra cellular fluid of the patient with at least one frequency within a range from about 0.5 kHz to about 200 kHz. and wherein the impedance circuitry is configured to determine a respiration of the patient.

4. The system of claim 1 wherein the processor system is configured to control a collection and transmission of data from the impedance circuitry.

5. The system of claim 1, further comprising at least one of electromyogram circuitry or an accelerometer mechanically coupled to a second adhesive patch to generate at least one of an electromyogram signal or an accelerometer signal when the second adhesive patch is adhered to the skin of the patient, wherein the at least one electromyogram signal or the accelerometer signal is communicated to the processor system.

6. The system of claim 1, further comprising an accelerometer mechanically coupled to a second adhesive patch to generate an accelerometer signal when the second adhesive patch is adhered to the skin of the patient, and wherein the second adhesive patch is configured to adhere to at least one of an ankle, a leg, a foot, or a jaw of the patient and wherein the processor system is configured to detect at least one of a restless leg or a bruxation of the patient in response to the accelerometer signal.

7. The system of claim 1 wherein the system comprises an accelerometer mechanically coupled to a second adhesive patch to generate an accelerometer signal when the second adhesive patch is adhered to the skin of the patient, and wherein the accelerometer is coupled to wireless communication circuitry supported with the second patch to transmit the accelerometer signal to the processor system.

8. The system of claim 1, further comprising at least one of electromyogram circuitry or an accelerometer mechanically coupled to at least one of the adhesive patch or a strap to generate at least one of an electromyogram signal or an accelerometer signal when the at least one of the adhesive patch or the strap is positioned on the patient, wherein the at least one electromyogram signal or the accelerometer signal is communicated to the processor system.

9. The system of claim 1, further comprising an accelerometer mechanically coupled to the adhesive patch to generate an accelerometer signal when the adhesive patch is positioned on the patient, and wherein the accelerometer is coupled to wireless communication circuitry supported with the adhesive patch to transmit the accelerometer signal to the processor system.

10. The system of claim 1, further comprising an accelerometer mechanically coupled to the adhesive patch to generate an accelerometer signal in response to at least one of an activity or a position of the patient when the adhesive patch is adhered to the skin of the patient and wherein the processor system is configured to determine that the patient is asleep in response to the accelerometer signal.

11. The system of claim 10 wherein the accelerometer comprises at least one of a piezoelectric accelerometer, capacitive accelerometer or electromechanical accelerometer and wherein the accelerometer comprises a 3-axis accelerometer to measure at least one of an inclination, a position, an orientation or acceleration of the patient in three dimensions.

12. The system of claim 10, further comprising:
    electrocardiogram circuitry coupled to at least two of the at least four electrodes to measure an electrocardiogram signal of the patient.

13. The system of claim 12 wherein the processor system is configured to determine that the patient is asleep in response to the accelerometer signal and the electrocardiogram signal.

14. The system of claim 12 wherein the processor system is configured to detect the sleep apnea and/or hypopnea in response to a heart rate variability from the electrocardiogram signal.

15. The system of claim 12 wherein the adhesive patch is mechanically coupled to the at least four electrodes, the impedance circuitry, the electrocardiogram circuitry, the accelerometer and at least one processor of the processor system, such that the adhesive patch is capable of supporting the at least four electrodes, the impedance circuitry, the electrocardiogram circuitry the accelerometer and the at least one processor when the adhesive patch is adhered to the skin of the patient.

16. The system of claim 1 further comprising wireless communication circuitry coupled to the impedance circuitry to transmit the impedance signal to a remote center with a communication protocol.

17. The system of claim 16, further comprising electrocardiogram circuitry coupled to at least two of the at least four electrodes to measure an electrocardiogram signal of the patient, wherein at least one processor of the processor system is supported with the adhesive patch and wherein the at least one processor is configured to determine the respiration rate from the impedance signal and a heart rate from the electrocardiogram signal.

18. The system of claim 17, wherein the wireless communication circuitry is configured to transmit at least one of the heart rate or the respiration rate to the remote center to determine an apnea hypopnea index.

19. The system of claim 1 further comprising wireless communication circuitry coupled to the impedance circuitry, wherein the wireless communication circuitry transmits the respiration rate to a remote center with a communication protocol.

20. The system of claim 19, further comprising an intermediate device, wherein the wireless communication circuitry transmits the respiration rate to the remote center via the intermediate device.

21. The system of claim 20 wherein the communication protocol comprises at least one of Bluetooth, Zigbee, WiFi, WiMax, IR, a cellular protocol, amplitude modulation or frequency modulation.

22. The system of claim 20 wherein the intermediate device comprises a data collection system to collect and/or store data from the wireless communication circuitry and wherein the data collection system is configured to communicate periodically with the remote center with wireless connection and/or wired communication.

23. The system of claim 20 wherein the communication protocol comprises a two way protocol such that the remote center is capable of issuing commands to control data collection.

24. The system of claim 1 wherein the adhesive patch comprises a breathable tape, in which the breathable tape comprises a breathable material with an adhesive.

25. The system of claim 1 further comprising a temperature sensor to generate a temperature signal, the temperature sensor coupled to the processor system to determine when the patient is asleep.

26. A method of monitoring a sleep apnea of a patient, the method comprising:
    adhering an adhesive patch to a skin of the patient to couple at least four electrodes to the skin of the patient;
    measuring an impedance signal of the patient with impedance circuitry coupled to the at least four electrodes;
    determining a respiration rate from the impedance signal to detect an apnea and/or hypopnea of the patient in response to the impedance signal; and
    providing information about the apnea and/or hypopnea to a decompensation prediction algorithm.

27. The method of claim 26, further comprising determining an apnea hypopnea index of the patient in response to the impedance signal, and providing the apnea hypopnea index to the decompensation prediction algorithm.

28. The method of claim 26, further comprising:
    generating an accelerometer signal with an accelerometer; and
    determining that the patient is asleep in response to the accelerometer signal.

29. The method of claim 26, further comprising:
    measuring an electrocardiogram signal of the patient with electrocardiogram circuitry coupled to at least two of the at least four electrodes; and
    measuring a signal from an accelerometer in response to at least one of an activity, a restless leg, a bruxation or a position of the patient.

30. The method of claim 29 wherein the adhesive patch supports the at least four electrodes, the impedance circuitry, the electrocardiogram circuitry and the accelerometer when the adhesive patch is adhered to the skin of the patient.

* * * * *